United States Patent
Nzike et al.

(10) Patent No.: US 10,309,387 B2
(45) Date of Patent: Jun. 4, 2019

(54) PERISTALTIC PUMP (71) Applicants: Sanofi-Aventis Deutschland GmbH, Frankfurt am Main (DE); Kevin Igor Youmbi Ngatchou, Mainz (DE)

(72) Inventors: Philippe Nzike, Frankfurt am Main (DE); Michael Schabbach, Frankfurt am Main (DE); Olaf Zeckai, Weinheim (DE); Meinolf Werner, Worms (DE); Ole Simonowsky, Blankenrath (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 15/383,925

(22) Filed: Dec. 19, 2016

(65) Prior Publication Data
US 2017/0096994 A1 Apr. 6, 2017

Related U.S. Application Data (63) Continuation of application No. 14/343,726, filed as application No. PCT/EP2012/068694 on Sep. 21, 2012, now Pat. No. 9,695,813.

(30) Foreign Application Priority Data

Sep. 21, 2011 (EP) .................................... 11182226

(51) Int. Cl.
*F04B 43/12* (2006.01)
*A61M 5/142* (2006.01)
*F04B 43/00* (2006.01)

(52) U.S. Cl.
CPC ..... *F04B 43/1223* (2013.01); *A61M 5/14228* (2013.01); *F04B 43/0072* (2013.01); *F04B 43/12* (2013.01)

(58) Field of Classification Search
CPC .. F04B 43/12; F04B 43/1223; F04B 43/1238; F04B 43/1246; F04B 43/1253; F04B 43/1261; F04B 43/1269; A61M 5/14228
See application file for complete search history.

(56) References Cited

U.S. PATENT DOCUMENTS

| 533,575 A | 2/1895 | Wilkens |
| 1,874,667 A * | 8/1932 | Wada ................. A61M 1/1037 222/209 |
| 2,483,924 A * | 10/1949 | Moulinier ............. A61M 5/142 210/416.1 |

(Continued)

FOREIGN PATENT DOCUMENTS

| DE | 19729612 A1 | 1/1999 |
| DE | 10246469 A1 | 4/2004 |

(Continued)

OTHER PUBLICATIONS

English Translation of Notice of Reasons for Rejection issued in Japanese Patent Application No. 2014-531251 dated Jul. 5, 2016.

*Primary Examiner* — Kenneth J Hansen
(74) *Attorney, Agent, or Firm* — McCarter & English, LLP (57) ABSTRACT

A peristaltic pump comprises a tube to transport a material in a transport direction and a conveying screw, which is configured to cause a transport of the material by causing a successive squeezing of the tube along the transport direction.

14 Claims, 4 Drawing Sheets

(56) References Cited

U.S. PATENT DOCUMENTS

| | | |
|---|---|---|
| 3,582,234 A * | 6/1971 | Isreeli .................. G01N 35/08 138/45 |
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,370,510 A | 12/1994 | Sinclair et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2009/0275916 A1 | 11/2009 | Harms et al. |

FOREIGN PATENT DOCUMENTS

| | | |
|---|---|---|
| EP | 0937471 A2 | 8/1999 |
| EP | 0937476 A2 | 8/1999 |
| GB | 369037 | 3/1932 |
| JP | H02-145681 A | 6/1990 |
| JP | 2007138786 A | 6/2007 |
| WO | 9938554 A1 | 8/1999 |
| WO | 0110484 A1 | 2/2001 |
| WO | 2005120387 A2 | 12/2005 |

* cited by examiner

PERISTALTIC PUMP

CROSS REFERENCE TO RELATED APPLICATIONS

The present application is a continuation of U.S. application Ser. No. 14/343,726 filed Mar. 7, 2014, which is a U.S. National Phase Application pursuant to 35 U.S.C. § 371 of International Application No. PCT/EP2012/068694 filed Sep. 21, 2012, which claims priority to European Patent Application No. 11182226.8 filed Sep. 21, 2011. The entire disclosure contents of these applications are herewith incorporated by reference into the present application.

FIELD OF INVENTION

The present disclosure relates to a peristaltic pump. Peristaltic pumps are configured to transport a material in a tube by squeezing the tube.

Peristaltic pumps are known from the prior art, as for example from the documents DE 10246469 A1 or DE 19729612 A1.

BACKGROUND

It is an object of the present invention to provide a peristaltic pump which shows improved properties.

SUMMARY

According to one aspect of the disclosure, a peristaltic pump is provided, comprising a tube and a conveying screw. The tube is configured to transport a material in a transport direction. The conveying screw is configured to cause a transport of the material by effecting a squeezing of the tube along the transport direction.

Preferably, the conveying screw effects a squeezing of the tube along the transport direction when it is rotated around a rotation axis. Preferably, the rotation of the conveying screw causes a movement of a squeezed patch of the tube in transport direction.

The peristaltic pump may be intended to be applied for medical use. Preferably, the peristaltic pump is configured to transport medical fluids. Preferably the peristaltic pump is configured to dispense small amounts of fluids. In particular, the pump may be used in the field of micro-fluidics. In a preferred embodiment, the peristaltic pump may transport a highly sensitive material. The material may be a medicament, for example insulin. As a further example, the pump may be configured as a dialysis pump to transport blood.

Preferably, the conveying screw is used as a pump head. A pump head may be an element, which by its movement may cause a squeezing of the tube. The conveying screw may comprise a screw thread. The conveying screw may be rotatable about a rotation axis, wherein a transport of a material in transport direction may be caused by a rotation of the screw thread around the rotation axis. The conveying screw may be an Archimedes screw. Preferably, the screw is fixed relative to a housing of the pump such that only a rotational movement of the screw about a rotation axis is enabled. In a preferred embodiment, the conveying screw is driven by an engine. In a preferred embodiment, the conveying screw and the engine are linked by gear wheels. The conveying screw may be manufactured with high precision and at a low cost.

A pitch of the screw thread of the conveying screw may be configured such that a relatively low speed of pumping may be achieved. Therefore, this kind of construction may be suitable for the pumping of small amounts of fluid. Preferably, the low speed of pumping may allow a gentle treatment of the material transported in the tube.

Preferably, a rotation axis of the conveying screw runs parallel to the tube. The conveying screw may be arranged with a distance to the tube.

Preferably, the conveying screw is operated at a constant driving speed. Thereby, a high accuracy of dosage may be achieved. Furthermore, a constant, nearly shock-free pumping may be achieved because of the constant driving speed. The constant driving speed may also lead to a high reproducibility of the pumping amount.

Preferably, the tube is arranged in a linear form along an axis. In a preferred embodiment, the tube is free of curved sections. Particularly, the tube may be configured such that it does not show any U-shaped sections. Thereby an adjustment of the tube in the peristaltic pump during an exchange of the tube may become easier and reproducible, since the handling and positioning of the tube may be easier. Thereby, the risk of misalignment of the tube may be reduced. This may lead to a higher dose accuracy and increase the safety when handling the peristaltic pump.

Preferably, the peristaltic pump of the present disclosure comprises at least one squeeze element. The squeeze element may be configured for squeezing the tube. When the squeeze element squeezes the tube, it may be arranged between the conveying screw and the tube. The squeeze element may be in contact with the tube and the conveying screw. Preferably, the peristaltic pump comprises a plurality of squeeze elements.

Preferably, the squeeze element is configured such that it may squeeze the tube and close it by that. In a preferred embodiment, the squeeze element is configured such that by squeezing the tube it displaces the material, which is transported in the tube, from the squeezed patch. The squeeze element may be configured such that low friction forces occur.

In a preferred embodiment, the squeeze element comprises a member which is configured to roll off on the tube. Thus an axial deformation of the tube by the squeeze element may be kept low.

In a preferred embodiment, the member may be configured as a ball.

Furthermore, the squeeze element may comprise a resilient member such as a spring. Preferably, the spring is configured to press the member which is configured to roll off on the tube onto the tube such that the member squeezes the tube and closes it by that. Preferably, the spring force of the spring is such that the tube is squeezed to closure, but not heavily loaded.

Preferably, the squeeze element comprises a carrier element. The carrier element may be in contact with the conveying screw, when the squeeze element is moved along the tube. In a preferred embodiment, the squeeze may be in contact with the screw thread of the conveying screw. In a preferred embodiment, the squeeze element may be configured to transmit a force from the screw thread of the conveying screw to a member, for example to a ball.

In a preferred embodiment, the peristaltic pump is configured such that a movement of the squeeze element in the transport direction is caused by a rotation of the conveying screw.

Preferably, the rotation of the conveying screw causes a movement of the squeeze element along the tube. Preferably, the movement of the squeeze element along the tube causes a squeezing of the tube such that a squeezed patch of the tube is moved in transport direction. Thereby, the transport of the material in transport direction is achieved. In a preferred embodiment, at least one squeeze element squeezes the tube at a particular time. Thereby, the squeeze element may serve as a valve, in order to inhibit a reflow of the material.

In particular, a screw thread of the conveying screw may be configured to move the squeeze element along the tube in transport direction by applying a force on the squeeze element. The carrier element may be configured such that the squeeze element may be coupled to the screw thread of the conveying screw.

In a further embodiment, the peristaltic pump may comprise a guide member for guiding the squeeze element. Preferably, the guide member comprises a circulation system.

The circulation system may comprise a circulating groove. The groove may be configured such that by following the groove, starting from a start position, the start position may be reached again. Preferably, the squeeze element is guided in the circulation system of the guide member.

Preferably, the squeeze element has a start position and an end position in the circulation system. Preferably, the pump is configured such that during operation of the pump the squeeze element is transported from the start position to the end position and back from the end position to the start position.

The start position may be a location in the circulation system where the squeeze element gets coupled to the screw thread of the conveying screw. The end position may be a location in the circulation system, where the squeeze element is released from the screw thread of the conveying screw. Preferably, the start position is a location at the tube where the squeeze element gets in contact with the tube. The end position may be a location at the tube where the squeeze element is allowed to leave the tube.

Preferably, the tube comprises a transport mechanism for transporting the squeeze element in the circulation system. Preferably, the squeeze element is transported from the start position to the end position by the rotation of the conveying screw. Preferably, the squeeze element is transported back from the end position to the start position by a back-transport mechanism. Preferably, the squeeze element is transported from the end position back to the start position in a way such that it is not in contact with the tube.

The back-transport mechanism may comprise a lever. The lever may be configured to release the squeeze element from the screw thread of the conveying screw.

Furthermore, the transport mechanism may comprise a lever spring. In a preferred embodiment, the lever is configured to be pre-tensioned by the lever spring. Particularly, the lever may be pre-tensioned by the lever spring when the squeeze element is at its end position. The lever may be pre-tensioned by the lever spring such that a movement of the lever is facilitated in order to release the squeeze element from the screw thread of the conveying screw.

The lever may be rotatable around a rotation axis. The rotation axis of the lever may be perpendicular to the rotation axis of the conveying screw. The lever may be fixed to the guide member, for example by a bolt. A rotation of the lever in a first rotational direction may be caused by the movement of the squeeze element. Preferably, the lever is rotated such that the lever spring is loaded. In a preferred embodiment, the lever spring may be loaded by the movement of the squeeze element, particularly when the squeeze element reaches its end position.

Preferably, when the squeeze element has reached the end position, the squeeze element may be allowed to leave the tube. In particular, the guide member may be configured such that a movement of the squeeze element away from the tube may be enabled. As an example, the circulation system may comprise a curve that leads the squeeze element away from the tube. Preferably, when the squeeze element has reached the end position, the lever spring may be allowed to relax. Preferably, a relaxation of the lever spring causes a rotation of the lever. In a preferred embodiment, the lever pushes the squeeze element away from the tube.

Preferably, a plurality of squeeze elements is guided in the circulation system. When one of the squeeze elements is pushed away from the tube, it may abut another squeeze element in the circulation system. Preferably, thereby, the other squeeze element is pushed towards the start position. Preferably, when one of the squeeze elements has reached the start position, it may be coupled to the screw thread of the conveying screw and be moved along the transport direction.

The peristaltic pump may comprise a first and a second squeeze element. The first and second squeeze elements are representatives for a plurality of squeeze elements. However, the number of the squeeze elements is not limited.

Preferably, when the first squeeze element is coupled to the screw thread of the conveying screw and moved along the tube in transport direction, the tube may be squeezed in a patch. Preferably, the squeezed patch may be moved along the tube in transport direction by the rotation of the conveying screw. Preferably, before the first squeeze element reaches the end position of the tube, the second squeeze element may be coupled to the screw thread of the conveying screw and be moved along the tube in the same way as the first squeeze element. Thus, at any time at least one squeeze element may close the tube and thereby inhibit a reflux of the material in a direction opposite to the transport direction.

When the squeeze element is moved along the tube, it may squeeze the tube in a patch of the tube. The squeezing of the tube may effect a displacement of the material in the tube from the patch which is squeezed. Thereby, an increased pressure is created in front of the squeeze element, respectively in front of the squeezed patch, such that the material in the tube is moved forward along the transport direction. As the squeeze element moves on along the tube, the tube may widen up to its original unsqueezed diameter behind the squeeze element, respectively behind the squeezed patch. The widening of the tube may cause a reduced inlet pressure in the tube.

The peristaltic pump may comprise a receptacle. Because of the reduced inlet pressure, material may be drawn into the tube from the receptacle. The receptacle may contain the material to be transported, for example a liquid material, in particular a liquid medicament.

In a preferred embodiment, the peristaltic pump comprises a main body and an exchange part configured to be attachable to the main body.

Preferably, the main body comprises a housing and the conveying screw. In a preferred embodiment, the main body comprises at least one squeeze element, a guide member, a lever and a lever spring. The receptacle may be located in the main body.

If the peristaltic pump is configured for medical use, certain elements of the peristaltic pump may have to be exchanged after use, before the peristaltic pump is reused again. Preferably, an exchange part makes this process simple and quick for a user.

The exchange part is preferably designed to be attached to and detached from the main body. The exchange part may contain several parts, for example the tube and one or more needles. The exchange part may be locked on the main body. Preferably, the exchange part is configured to be attached and detached to the main body in a simple manner. There may be positioning elements at the main body in order to align the exchange part correctly, and safety elements, for example snap arms, to fix the exchange part during insertion. The exchange part may be configured to carry elements of the peristaltic pump which have to be exchanged periodically. Preferably, the elements which are carried by the exchange part are pre-assembled at the exchange part. This may make the exchange of the exchange part very simple for the user. Preferably, the exchange part is configured to be a disposable element being configured to be detached from the main body of the pump and replaced by a new, unused element.

In one embodiment, it may be possible to exchange the elements of the exchange part individually, for example one needle or the tube, and reuse the remaining elements of the exchange part.

Preferably, the exchange part comprises a tube guide for guiding the tube.

A tube guide may be a guide along which or in which the tube may run. The tube may be attached to the tube guide. Preferably, the tube guide comprises a longitudinal groove, in which the tube may run. Preferably, by means of the tube guide, the position of the tube in the pump is determined. Preferably, the tube guide enables that an accurate insertion and adjustment of the tube is simple and quick. In a preferred embodiment, the tube is positioned between the tube guide and a squeeze element. In a further embodiment, the tube may be positioned between the tube guide and the conveying screw.

Preferably, when the exchange part is detached from the main body, the tube is removed from the peristaltic pump together with the exchange part. Preferably, the tube is located in the exchange part in a way that when the exchange part is attached to the main body, the tube is positioned correctly relative to the conveying screw. For this aim, the main body may comprise positioning elements, so that the exchange part may be aligned properly.

The peristaltic pump may comprise at least one needle. As an example, the exchange part may be configured to carry at least one needle.

In particular, the needle may be configured to dispense the material, for example a fluid, to a tissue. The needle may be located such that material can flow from the tube into the needle. The needle may be positioned at an end of the exchange part which is faced away from a receptacle.

Additionally or alternatively, the peristaltic pump may comprise at least one needle by which the tube is provided with new material. Preferably, the needle may be attached to the exchange part. The needle may be positioned at an end of the exchange part which is faced towards a receptacle. The needle may be configured to be inserted into the receptacle. Preferably, the needle may be connected with the tube such that material can flow from the receptacle into the tube.

In a preferred embodiment, the peristaltic pump may comprise a first and a second needle. As an example, the exchange part may be configured to carry a first and a second needle. The first needle may be configured to dispense the material and the second needle may be configured to provide the tube with new material.

In a further embodiment, the exchange part may comprise at least one screw thread for attaching and detaching an exchangeable needle. In this case, at least one of the needles may be exchanged individually.

In one embodiment the pump may be configured such that, in order to enable a detachment of the exchange part, a receptacle has to be removed from the main body first. After that, the exchange part may be enabled to be detached from the main body. The receptacle may be removed in a direction parallel to the tube. When the receptacle has been removed, the exchange part may be removed in a direction perpendicular to the tube. Alternatively, the exchange part may be removed in a direction parallel to the tube.

After replacing the exchange part, a new receptacle may be inserted into the pump. During insertion of the receptacle, a needle may be pierced into the receptacle.

In a further embodiment, the pump may be configured such that, in order to enable a detachment of the exchange part, the receptacle may not have to be removed. In this embodiment, a needle attached to the exchange part may be pierced into, respectively pulled out of the receptacle while the exchange part is replaced. In this embodiment, both components, namely the exchange part and the receptacle may be designed such that their moving directions during their detachment from the main body are parallel to each other. In this case the sequence of replacement of receptacle and exchange part may be unimportant, since the exchange part and the receptacle may be removed independently from each other.

When the new exchange part is attached to the main body, the exchange part may move towards the receptacle parallel to a longitudinal axis of the receptacle during insertion, such that a needle of the exchange part may move towards a dispensing end of the receptacle. In particular, during an attachment of the exchange part, the needle may be pierced into the receptacle. If a receptacle is replaced in a state where an exchange part is attached to the main body, during replacement the receptacle may move towards the exchange part parallel to a longitudinal axis such that the receptacle may meet the needle. Thereby, the needle may be pierced into the receptacle.

The term "medical fluid", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Further features, refinements and expediencies become apparent from the following description of the exemplary embodiments in connection with the figures.

Like elements, elements of the same kind and identically acting elements are provided with the same reference numerals in the figures.

DETAILED DESCRIPTION

Figure 1:
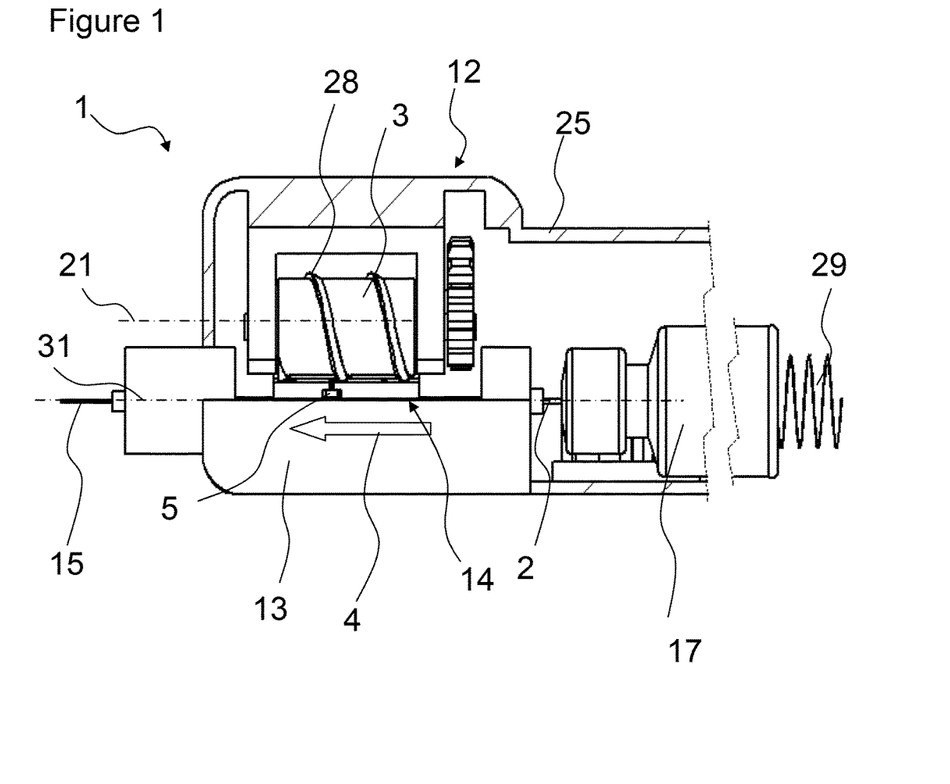
FIG. 1 shows a side view of an exemplary embodiment of a peristaltic pump.

FIG. 1 shows a peristaltic pump 1 comprising a tube 2 and a conveying screw 3. For clarity reasons, parts of a housing 25 of the pump 1 are cut away in this Figure. The peristaltic pump 1 is configured to transport a material. The material to be transported is moved in the tube 2 along a transport direction 4. The material may be for example insulin. Preferably, the material is a medical fluid. The peristaltic pump 1 is particularly suitable for microfluidic applications. Particularly, the peristaltic pump 1 may be configured to dispense small amounts of fluids.

The conveying screw 3 is configured to cause a transport of the material by causing a squeezing of the tube 2 along the transport direction 4. In particular, the conveying screw 3 may effect a squeezing of the tube 2 by rotating around a rotation axis 21. A squeeze element 5 may be arranged between the conveying screw 3 and the tube 2, being transported by the conveying screw 3 along the tube 2 and being configured to squeeze the tube 2.

The tube 2 may be of an elastic material. The tube 2 is arranged in a linear form. The tube 2 runs along an axis 31 parallel to the rotation axis 21 of the conveying screw 3. Particularly, the tube 2 does not show any curved or U-shaped sections. The tube 2 may run linearly in a tube guide 14, which is integrated in an exchange part 13.

The exchange part 13 is attached to a main body 12. The exchange part 13 is configured such that it may be easily attached to and detached from the main body 12. The main body 12 comprises the housing 25 and the conveying screw 3. A receptacle 17 is located in the main body 12. The receptacle 17 contains the material to be transported.

The exchange part 13 is configured to carry a needle 15, which is configured to dispense a material from the peristaltic pump 1. Another needle 16 (see FIG. 2), may be provided to be inserted into the receptacle 17.

The receptacle 17 may comprise a piston. The piston may be axially movable in the receptacle 17. A spring 29 may exert a force on the piston to facilitate a movement of the piston. Thereby, no air pockets may occur in the receptacle 17 when material is drawn from the receptacle 17 into the tube 2.

The exchange part 13 provides an easy and fast way to substitute the elements of the peristaltic pump 1 which should be sterile before a use of the peristaltic pump 1, namely the needles 15, 16 and the tube 2.

The exchange part 13 may be locked to the main body 14 by a flap. The flap may have to be opened in order to detach the exchange part 13 from the main body 14. The flap may close the main body 12 in order to inhibit that dust or other contaminants may invade into the pump 1.

Figure 2:
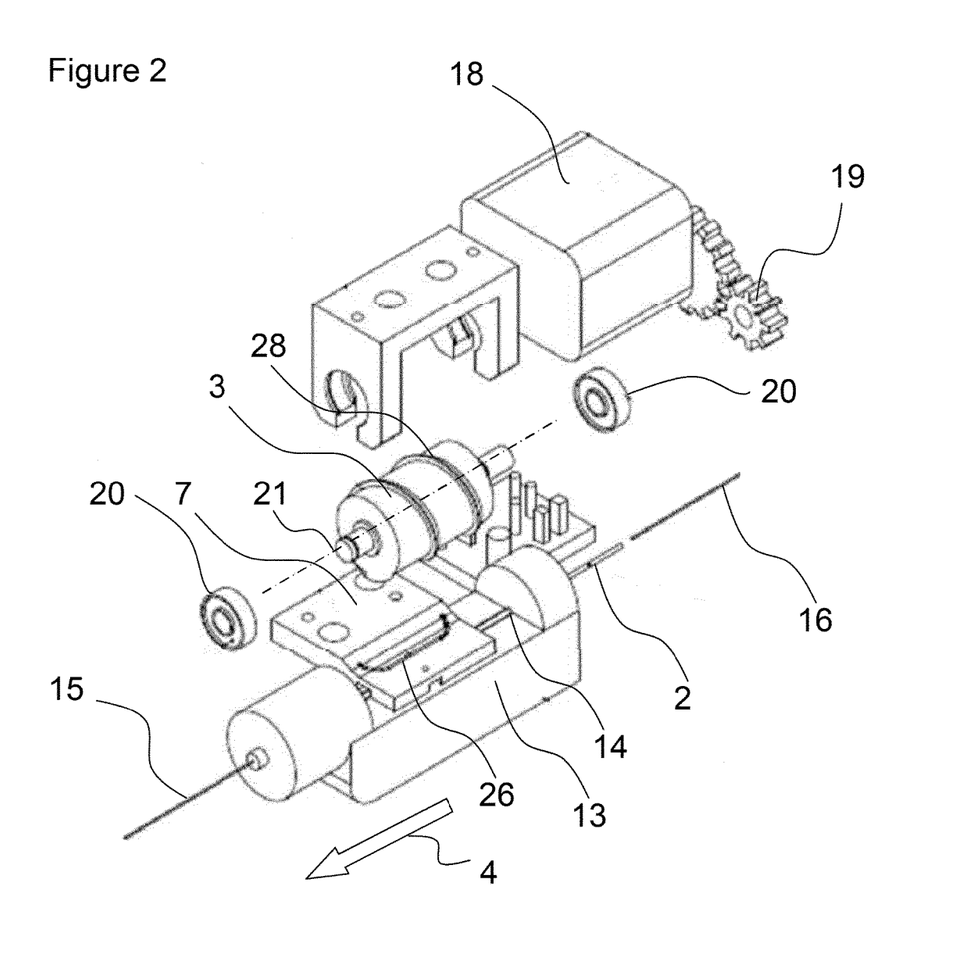
FIG. 2 shows an exploded view of parts of the peristaltic pump of FIG. 1.

FIG. 2 shows an exploded view of the peristaltic pump 1 of FIG. 1. The conveying screw 3 is supported by two bearings 20. The conveying screw 3 is driven by an engine 18. Gear wheels 19 are provided as intermediate elements between the engine 18 and the conveying screw 3. A guide member 7 is arranged between the exchange part 13 and the conveying screw 3. The guide member 7 comprises a cut-out for the tube 2, such that the tube 2 may run through the guide member 7. The guide member 7 is configured to guide the movement of a squeeze element 5 (see FIG. 1). The guide member 7 comprises a circulation system 26. The circulation system 26 may be configured as a circulating groove. The squeeze element 5 (see FIG. 1) may be guided in the circulation system 26.

Figures 3A, 3B:
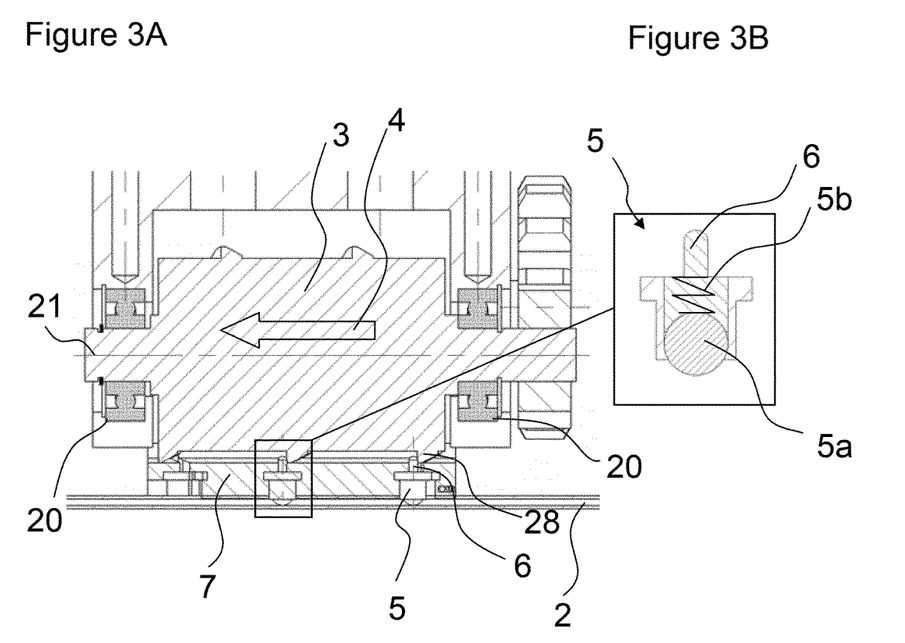
FIG. 3A shows a cross-sectional side view of an exemplary embodiment of the peristaltic pump of FIG. 1.
FIG. 3B shows a detailed sectional view of a squeeze element.

FIG. 3A shows a sectional side view of the peristaltic pump 1 of FIG. 1. It shows the conveying screw 3, which is supported on both sides by the bearings 20 and which is able to rotate around a rotation axis 21. Furthermore, the peristaltic pump 1 comprises at least one squeeze element 5. The squeeze element 5 is guided in the circulation system 26 of the guide member 7.

The rotation of the conveying screw 3 may cause a movement of the squeeze element 5 along the tube 2 in transport direction 4. The conveying screw 3 comprises a screw thread 28, which is configured such that it moves the squeeze element 5 along the tube in a transport direction 4 during the rotation of the conveying screw 3. During the movement of the squeeze element 5 along the tube 2, the squeeze element 5 squeezes the tube 2 in a patch. As the squeeze element 5 moves along the transport direction 4, the squeezed patch also moves in transport direction 4.

Preferably, when the squeeze element 5 squeezes the tube 2, the squeeze element 5 is located between the conveying screw 3 and the tube 2. The squeeze element 5 comprises a carrier element 6, which is in contact with the screw thread 28 of the conveying screw 3 when the squeeze element 5 is moved along the tube 2. In a preferred embodiment, the pump 1 comprises a plurality of squeeze elements 5.

When the squeeze element 5 is moved along the tube 2, the squeeze element 5 may squeeze the tube 2 such that it closes the tube 2 in one patch of the tube 2. The material may be displaced from the squeezed patch of the tube 2. Thereby, an overpressure may be created in front of the squeeze element 5. Thereby, the material may be moved forward along the transport direction 4. When the squeeze element 5 moves on along the tube 2, the tube 2 is not squeezed anymore at the backside of the squeeze element 5. The backside of the squeeze element 5 is the side which is faced towards the receptacle 17. Thus, the tube 2 may widen to its original, unsqueezed diameter at the backside of the squeeze element 5. The widening of the tube 2 may cause an inlet pressure in the tube 2. Thereby, new material may be drawn from the receptacle 17 into the tube 2.

Preferably, at least one squeeze element 5 is always squeezing the tube 2 such that the tube 2 is closed, such that a backflow of the material in a direction opposite to the transport direction 4 is inhibited. Preferably, at least two squeeze elements 5 are transported along the tube 2 at a particular time. The squeeze elements 5 may serve as valves.

FIG. 3B shows a detailed view of the squeeze element 5. The squeeze element 5 comprises a member 5*a* configured to roll off on the tube 2 and a spring 5*b*. The member 5*a* may be a ball. The spring 5*b* may press the ball onto the tube 2 such that the pressure of the ball is high enough to squeeze the tube 2 until it is closed. The ball is configured to roll off on the tube 2.

Figure 4:
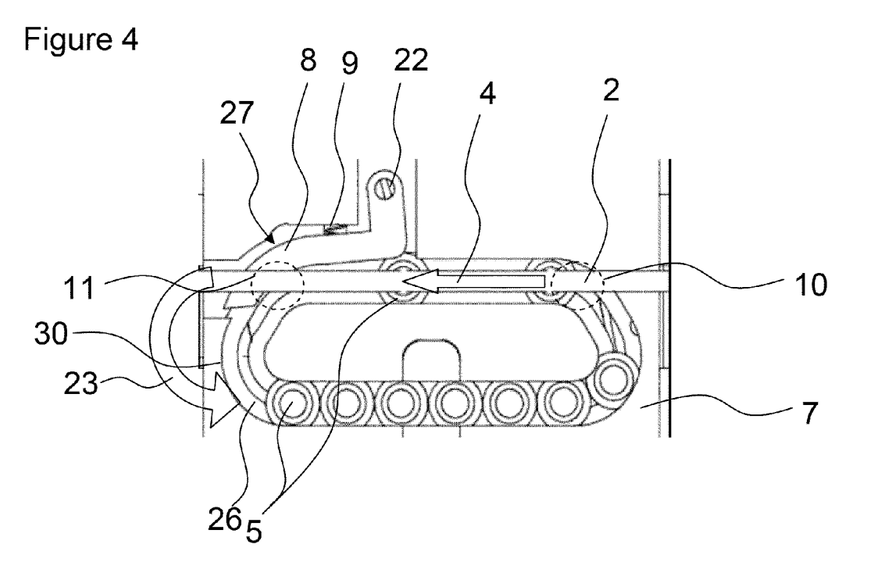
FIG. 4 shows a bottom view of a guide member and squeeze elements in the peristaltic pump of FIG. 1.

FIG. 4 shows a bottom view of the guide member 7 which is configured to guide at least one squeeze element 5. The guide member 7 comprises a circulation system 26 in which the squeeze element 5 may circulate from a start position 10 to an end position 11 and back to the start position 10. The squeeze element 5 may be transported along the tube 2 from the start position 10 to the end position 11 by the conveying screw 3, in particular by the screw thread 28 of the conveying screw 3. The start position 10 may be a location in the circulation system 26 where the squeeze element 5 gets picked up by screw thread 28 of the conveying screw 3. In an exemplary embodiment, the start position 10 may be at a patch of the tube 2 where the squeeze element 5 gets in contact with the tube 2. The squeeze element 5 is moved along the tube 2 until it reaches the end position 11. The end position 11 may be a patch of the tube 2 where the squeeze element 5 leaves the tube 2. When the squeeze element 5 has reached the end position 11, it may be released from the screw thread 28 of the conveying screw 3.

In particular, when the squeeze element 5 has reached the end position 11, it is transported back to the start position 10 in the circulation system 26 of the guide member 7. In order to facilitate the transport of the squeeze element 5 from the end position 11 to the start position 10, a back-transport mechanism 27 is provided.

The back-transport mechanism 27 comprises a lever 8. The lever 8 may be pre-tensioned by a lever spring 9, when the squeeze element 5 is at its end position 11. The lever may be pivot-mounted, for example on a bolt 22. A tensioning, for example by a compression of the lever spring 9, may be caused by the squeeze element 5. During the transport of the squeeze element 5 from the start position 10 to the end position 11, particularly when the squeeze element 5 reaches its end position 11, the lever 8 may be rotated around the bolt 22 such that the lever spring 9 is compressed. Particularly, the squeeze element 5 may move the lever 8 and thereby the lever 8 may compress the lever spring 9. When the squeeze element 5 has reached the end position 11, the squeeze element 5 may be allowed to leave the tube 2 since the circulation system 26 comprises a curve 30 that leads away from the tube 2. When the squeeze element 5 is allowed to leave the tube 2, the lever spring 9 may be allowed to relax, such that the lever spring 9 causes a movement of the lever 8. The movement of the lever 8 is such that the lever 8 pushes the squeeze element 5 away from the tube 2.

The lever 8 may cause a movement of the squeeze element 5 in a circulation direction 23 of the of the circulation system 26. The squeeze element 5 is moved back towards the start position 10 in the circulation system 26. Preferably, during the transport of the squeeze element 5 back to the start position 10, the squeeze element 5 is not in contact with the tube 2.

Preferably, the guide member 7 is configured such that it may guide a plurality of squeeze elements 5 from the end position 11 to the start position 10. When one squeeze element 5 is pushed away from the end position 11 by the lever 8, it may abut another squeeze element 5, such that one squeeze element 5 pushes another squeeze element 5 in the circulation direction 23. When one squeeze element 5 has reached the start position 10, it is picked up by the screw thread 28 of the conveying screw 3.

Figure 5:
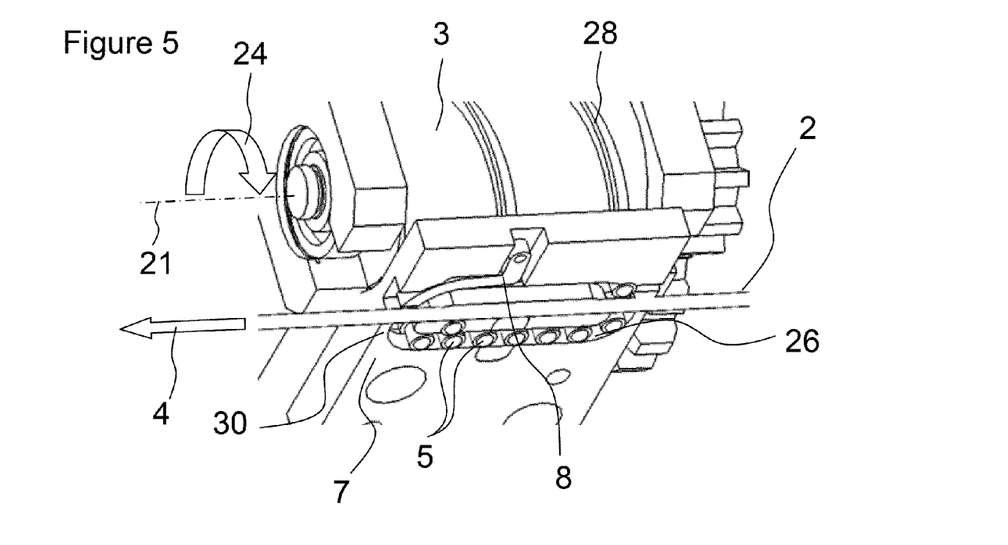
FIG. 5 shows a perspective view of parts of the pump of FIG. 1.

FIG. 5 shows a perspective view of parts of the peristaltic pump 1 of FIG. 1. The conveying screw 3 is rotated around the rotation axis 21 in the direction 24. Thereby, a movement of at least one of the squeeze elements 5 along the tube 2 is caused, such that the tube 2 is squeezed along the transport direction 4.

We claim:

1. A peristaltic pump, comprising:
   a tube to transport a material in a transport direction aligned with a longitudinal axis of the tube;
   a conveying screw configured to cause a transport of the material by effecting a squeezing of the tube along the transport direction; and
   at least one squeeze element configured to squeeze at least a portion of the tube when the at least one squeeze element is arranged between the conveying screw and the tube,
   the peristaltic pump being configured such that a rotation of the conveying screw causes movement of the at least one squeeze element in a direction substantially parallel to the transport direction when the at least one squeeze element is arranged between the conveying screw and the tube.

2. The peristaltic pump of claim 1, wherein the at least one squeeze element comprises a member configured to roll off on the tube.

3. The peristaltic pump of claim 1, wherein the at least one squeeze element comprises a carrier element that is in contact with the conveying screw when the at least one squeeze element squeezes the tube.

4. The peristaltic pump of claim 1, wherein the conveying screw comprises a screw thread configured to move the at least one squeeze element along the tube by applying a force on the at least one squeeze element.

5. The peristaltic pump of claim 1, further comprising a guide member for guiding the at least one squeeze element, the guide member including a circulation system.

6. The peristaltic pump of claim 5, wherein the at least one squeeze element has a start position and an end position in the circulation system and wherein the pump is configured such that during operation of the pump, the at least one squeeze element is transported from the start position to the end position, and from the end position back to the start position.

7. The peristaltic pump of claim 6, wherein the at least one squeeze element is transportable from the start position to the end position by the rotation of the conveying screw, and transportable from the end position back to the start position by a back-transport mechanism.

8. The peristaltic pump of claim 7, wherein the back-transport mechanism comprises a lever.

9. The peristaltic pump of claim 8, wherein the conveying screw comprises a screw thread, and wherein the lever is configured to be pre-tensioned by a lever spring in order to release the at least one squeeze element from the screw thread of the conveying screw when the at least one squeeze element is in the end position.

10. The peristaltic pump of claim 1 further comprising a main body and an exchange part configured to be attachable to the main body.

11. The peristaltic pump of claim 10, wherein the exchange part comprises a tube guide for guiding the tube.

12. The peristaltic pump of claim 1 further comprising at least one needle.

13. The peristaltic pump of claim 1, wherein the pump is configured to transport medical fluids.

14. The peristaltic pump of claim 1, wherein the transport direction is substantially parallel to a rotation axis of the conveying screw.

* * * * *

UNITED STATES PATENT AND TRADEMARK OFFICE
CERTIFICATE OF CORRECTION

PATENT NO. : 10,309,387 B2  
APPLICATION NO. : 15/383925  
DATED : June 4, 2019  
INVENTOR(S) : Philippe Nzike et al.

Page 1 of 1

It is certified that error appears in the above-identified patent and that said Letters Patent is hereby corrected as shown below:

On the Title Page

At item [71], Applicant: Delete "; Kevin Igor Youmbi Ngatchou, Mainz (DE)".

Signed and Sealed this  
Twelfth Day of November, 2019

Andrei Iancu  
*Director of the United States Patent and Trademark Office*